United States Patent
Studer

(10) Patent No.: US 8,516,883 B2
(45) Date of Patent: Aug. 27, 2013

(54) DEVICE AND METHOD FOR DETERMINING THE FILL LEVEL OF A FLEXIBLE MEDICINE RESERVOIR

(75) Inventor: Gerald Studer, Flaach (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/617,948

(22) Filed: Sep. 14, 2012

(65) Prior Publication Data

US 2013/0042678 A1 Feb. 21, 2013

Related U.S. Application Data

(63) Continuation of application No. 12/943,405, filed on Nov. 10, 2010, now Pat. No. 8,286,484.

(30) Foreign Application Priority Data

Nov. 11, 2009 (EP) ..................................... 09175634

(51) Int. Cl.
*G01F 23/00* (2006.01)
(52) U.S. Cl.
USPC ....................................................... 73/304 R
(58) Field of Classification Search
USPC ........................................ 73/304 R; 604/246
See application file for complete search history.

(56) References Cited

U.S. PATENT DOCUMENTS

| 5,098,409 A * | 3/1992 | Stock ............................ 604/246 |
| 6,315,769 B1 * | 11/2001 | Peer et al. ................... 604/891.1 |
| 2002/0120236 A1 * | 8/2002 | Diaz et al. ...................... 604/151 |
| 2007/0293817 A1 * | 12/2007 | Feng et al. ....................... 604/65 |

FOREIGN PATENT DOCUMENTS

| EP | 1818664 A1 | 8/2007 |
| EP | 1970677 A1 | 9/2008 |

OTHER PUBLICATIONS

European Search report, issued in priority EP Application 09175634.6, mailed May 28, 2010.
Analog Microelectronics GmbH, "CAV424—C/U transducer IC with adjustable output voltage", analog microelectronics integrated circuits, http://www.analogmicro.de, pp. 1-16, Jul. 2007.

* cited by examiner

*Primary Examiner* — Lisa Caputo
*Assistant Examiner* — Jamel Williams
(74) *Attorney, Agent, or Firm* — Dinsmore & Shohl LLP

(57) ABSTRACT

Included are systems and methods for determining a fill level of an inflow-less flexible medicine reservoir as a source for medicine, where the inflow-less flexible medicine reservoir has a monotonically decreasing fill level. Some embodiments of a device include a stop surface designed and arranged such that the stop surface contacts the inflow-less flexible medicine reservoir while the inflow-less flexible medicine reservoir is filled above a predetermined level. Similarly, some embodiments of the device additionally include a release detector that generates an output signal indicative of contact between the stop surface and the inflow-less flexible medicine reservoir being released and a processing unit for determining the fill level of the inflow-less flexible medicine reservoir from an output signal of the release detector.

33 Claims, 12 Drawing Sheets

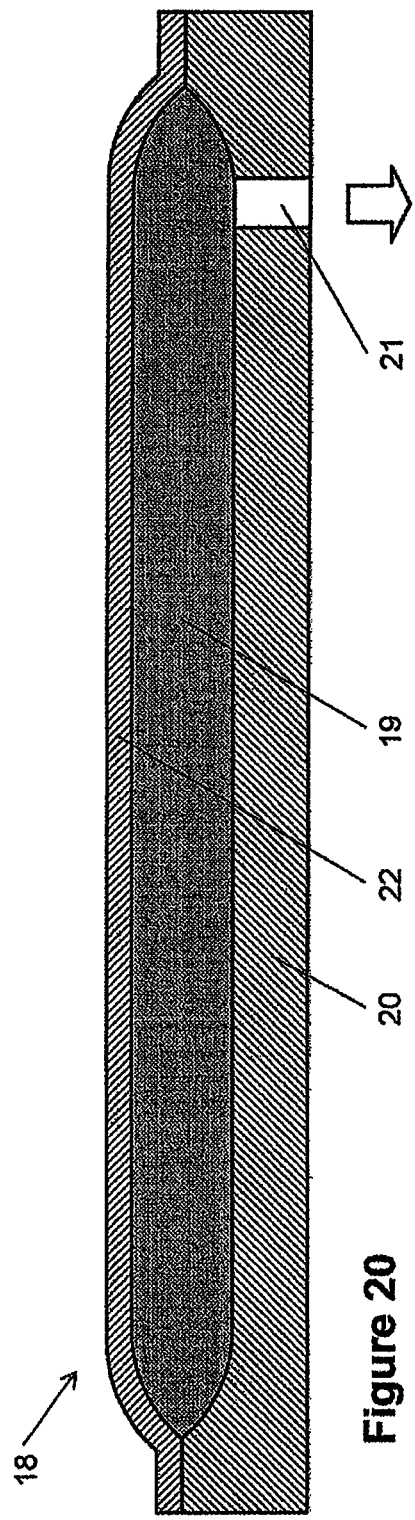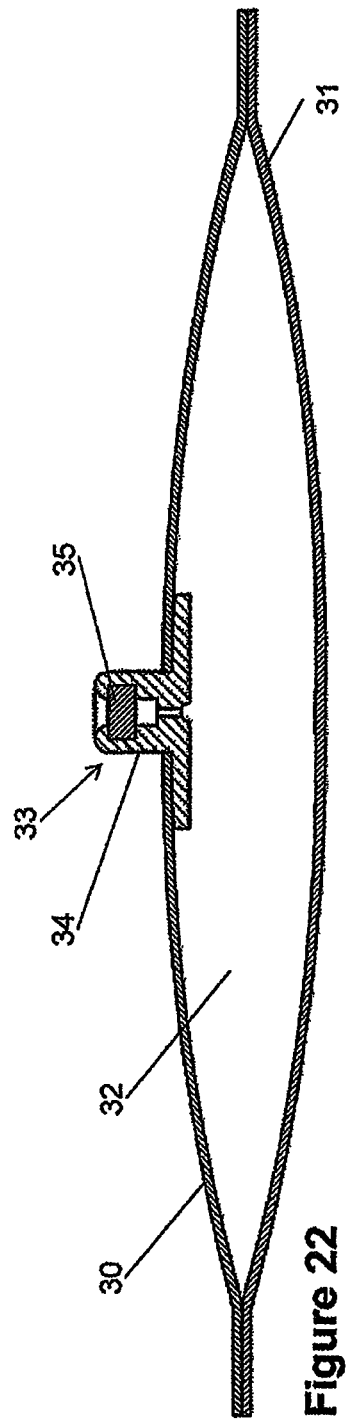

DEVICE AND METHOD FOR DETERMINING THE FILL LEVEL OF A FLEXIBLE MEDICINE RESERVOIR

CROSS REFERENCE TO RELATED APPLICATION

This application is a continuation of U.S. patent application Ser. No. 12/943,405 filed Nov. 10, 2010, which claims the priority to European Application Number EP09175634.6, filed Nov. 11, 2009, which is hereby incorporated by reference in its entirety.

TECHNICAL FIELD

This disclosure relates generally to a device and a method for determining the fill level of a flexible medicine reservoir and a medical infusion device comprising such a device.

BACKGROUND

Many current medical infusion devices, such as those for delivering insulin, usually include a rigid container, such as a medical reservoir for the medicine. The containers are generally syringes or other containers having a plunger for administering the medicine. According to standards for medical electrical equipment, it is generally desired to cause an alert if a fill level of the medicine reservoir falls to a certain level. For a rigid medicine container, the fill level can be determined from the position of the plunger within the container. However, medical infusion devices with rigid containers are often limited to the design of the infusion device and, for a given maximum size of the infusion device, are limited in the amount of medicine they can carry.

These design drawbacks can be overcome by using a flexible medicine reservoir that can better utilize the available space within the infusion device. With a flexible medicine reservoir, such as a bag, it is favorable not to push the medicine out of the container by forcing a plunger forwards, but to pump the medicine out the container via suction pressure. Such a pump may also be utilized as a dosing device. This concept is called downstream dosing. The pump fills its chamber from the medicine reservoir and then empties the chamber by administering the medicine in small increments of the chamber volume. This cycle is then repeated. Within this document, the flexible medicine reservoir is also referenced to as medicine reservoir, flexible reservoir or just reservoir, thereby always meaning the same entity.

With a flexible medicine reservoir, there is generally no plunger whose position could be used for determining the fill level of the medicine reservoir. One possibility for determining the fill level of the medicine reservoir would be to integrate the amount of delivered medicine. But such a solution has the drawback that only the amount of medicine taken from the reservoir can be determined, but not the amount of remaining medicine. This is an issue if the initial fill level of the reservoir can vary. In addition, there can be a difference between the amount of medicine to be delivered and the actual amount delivered, which sums up during integration. This means that the medical infusion device could cause an alert even though the reservoir is not emptied to the level where an alert should be generated, or even worse, the medical infusion device could not cause an alert even though the reservoir is emptied below that level and may even be completely empty.

SUMMARY

Included are systems and methods for determining a fill level of an inflow-less flexible medicine reservoir as a source for medicine, where the inflow-less flexible medicine reservoir has a monotonically decreasing fill level. Some embodiments of a device include a stop surface designed and arranged such that the stop surface contacts the inflow-less flexible medicine reservoir while the inflow-less flexible medicine reservoir is filled above a predetermined level. Similarly, some embodiments of the device additionally include a release detector that generates an output signal indicative of contact between the stop surface and the inflow-less flexible medicine reservoir being released and a processing unit for determining the fill level of the inflow-less flexible medicine reservoir from an output signal of the release detector.

Also included are embodiments of a method for determining a fill level of an inflow-less flexible medicine reservoir as a source for medicine, the inflow-less flexible medicine reservoir having a monotonically decreasing fill level. In some embodiments, the method includes determining when a threshold fill level of the inflow-less flexible medicine reservoir has been reached and determining an amount of medicine taken from the inflow-less flexible medicine reservoir since the threshold fill level has been reached. Similarly, some embodiments include calculating the fill level by subtracting the amount of medicine taken from the inflow-less flexible medicine reservoir from the threshold fill level.

BRIEF DESCRIPTION OF THE DRAWINGS

The contents of this disclosure will now be illustrated on the basis of different embodiments. All the features described in connection with the figures and/or shown in the figures form part of this disclosure.

FIG. 20 depicts an exemplary reservoir, according to embodiments disclosed herein;

FIG. 22 depicts a third exemplary reservoir, according to embodiments disclosed herein.

DETAILED DESCRIPTION

Figure 1:
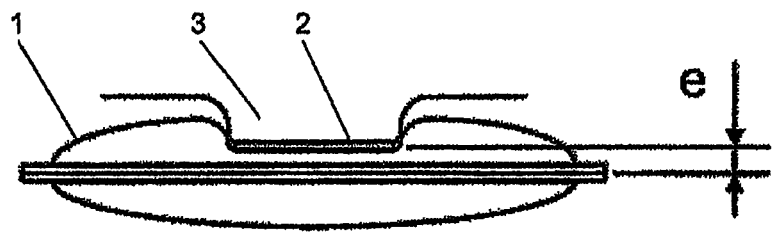
FIG. 1 depicts an arrangement with a plurality of electrodes located on a ram pushing into a flexible medicine reservoir, according to embodiments disclosed herein.

The present disclosure relates to a device and a method for determining the fill level of a flexible medicine reservoir and a medical infusion device comprising such a device. Some embodiments may include a device and a method for determining the fill level of a flexible medicine reservoir, or at least for determining if the fill level of a flexible medicine reservoir has fallen to or below a threshold level. As used herein, the term "medicine" encompasses any drug-containing flowable medicine, or therapeutic or diagnostic liquid, which can be delivered to a patient. In particular, this term encompasses insulin preparations ready for administration.

Embodiments disclosed herein include a flexible medicine reservoir include a reservoir with a preferably monotonically decreasing fill level of contained medicine during normal operation, such as e.g. during an infusion operation. In particular, the volume of the flexible medicine reservoir may be monotonically decreasing. In some embodiments, the reservoir only includes one or more outflows, but no inflow. This means that in these embodiments, the flexible medicine reservoir is a pure source of medicine that is not refilled during regular operation. A dedicated filling port, however, may be provided that is used for filling the reservoir prior to the drug infusion and may in principle also be used for re-filling. Such filling or re-filling, however, may be separate from the medicine infusion and is carried out in a negligible or at a different time as compared to infusion. The term "inflow-less" can be interpreted as having no inflow during normal operation but does not exclude that one or more re-filling openings are provided.

The fill level therefore represents the remaining amount of medicine that can be delivered by the infusion device (for example, by the ultimate reserve of the infusion device). The flexible medicine reservoir is not an intermediate repository in a chain of repositories and not a conduit. Preferably, the reservoir ends with its outflow and does not comprise a conduit for conveying the medicine to a destination. Further, the reservoir is preferably exchangeable, for example for replacing an empty or almost empty reservoir with a full reservoir. In some embodiments, the reservoir does not have a tube-like shape and, in particular, does not have a circular diameter along its length or longitudinal extension. However, the reservoir may have a base surface or footprint that is circular. Additionally, the cross-sectional area of the reservoir may vary when the reservoir is filled or gradually emptied. As an example, the flexible medicine reservoir may have at least one wall. The at least one wall of the reservoir is joined to form a storage volume for the medicine.

The reservoir may be cushion-like or have a disk-like shape and be realized as pouch or bag. The footprint may, for example, be circular, elliptical or rectangular. The dimensions or diameter of the footprint are may be significantly larger as compared to the lateral direction or thickness of the reservoir.

The device for determining the fill level of an inflow-less flexible medicine reservoir according to the present disclosure includes a stop surface designed and arranged such that the stop surface contacts the flexible medicine reservoir while the reservoir is filled above a predetermined level; a release detector arranged and configured to generate an output signal indicative of contact between the stop surface and the flexible medicine reservoir being released; and a processing unit for determining the fill level of the flexible medicine reservoir from the output signal of the release detector.

The stop surface can be a sensitive part of the release detector, a surface connected to the sensitive part of the release detector or a surface covering the sensitive part of the release detector. The sensitive part, or sensitive area, is a part or area of the release detector which is sensitive for a physical value and which is used for generating the output signal.

The stop surface is completely in contact with the flexible medicine reservoir as long as the reservoir is filled above a predetermined level. This means that the whole area of the stop surface is in contact with the flexible medicine reservoir. The predetermined level represents an absolute amount of medicine left in the reservoir. This means that a fill level of the reservoir can be determined before the reservoir is actually empty. Therefore, an optional warning can be provided to the user that a critical fill level is approaching, but not yet reached. This leaves enough time to provide a fresh filled medicine reservoir.

Once the fill level falls below the predetermined level, the contact between the stop surface and the flexible medicine reservoir starts to release. This means that the contact area between the stop surface and the reservoir remains constant until the predetermined fill level is reached, then progressively decreases, for example until the size of the area is zero, which means that there is no remaining contact between the stop surface and the reservoir.

Additionally, in some embodiments, the stop surface is only in punctiform contact with the reservoir. This means that the stop surface is in contact only with a part of the surface of the reservoir, for example never more than 50%, 25%, 20%, 10%, 5%, 2% or 1% of the reservoir surface. Further, in some embodiments, the stop surface has a convex shape. This means that the stop surface does not lose contact with the flexible medicine reservoir instantly when the reservoir reaches a certain fill level, but the contact area decreases this with a decreasing fill level of the reservoir.

In one implementation, the stop surface deforms the flexible medicine reservoir as long as the fill level of the reservoir is above a predetermined fill level. This means that the stop surface pushes into the reservoir such that the reservoir swells over the boundary of the stop surface. If the stop surface or any other component is described within this document as having a certain effect, this means that the stop surface or the component is designed and/or located to achieve this effect. Preferably, the stop surface contacts the flexible medicine reservoir spaced apart from the outflow or outflows of the reservoir. In particular, the stop surface contacts the reservoir at a reservoir wall or part of the reservoir wall adjacent to or opposite to the wall or area or part of the wall having the outlet or outlets.

In some embodiments, the stop surface is provided at a part of the reservoir wall where a change of the filling level of the reservoir can be detected and preferably has a larger or maximum effect on the shape of the reservoir or causes a larger or maximum deformation of the reservoir wall or outside than at another or adjacent position at the reservoir wall.

Preferably, no flow of a substance or medicine (or only a small flow of a substance or medicine) passes the stop surface or reservoir wall while the fill level of the reservoir decreases. In particular, the flow passing the stop surface is less than the flow through the outflow (if the reservoir has exactly one outflow) or the entirety of outflows (if the reservoir has a plurality of outflows) of the reservoir.

Further, the stop surface contacts a storage volume of the reservoir and not a conduit connected to the storage volume. So if a conduit such as an outflow conduit is considered as belonging to the flexible medicine reservoir, determination of the fill level is not performed in an area corresponding to the conduit, but in an area corresponding to the storage volume.

If the reservoir is exchangeable, the stop surface preferably contacts an exchangeable part of the reservoir. In particular, some embodiments of the stop surface do not contact a conduit which remains within the medical infusion device when the reservoir is replaced. The output signal of the release detector being indicative of the contact between the stop surface and the flexible medicine reservoir being released means that the signal indicates that (i) the contact starts to release at the beginning of the release process, (ii) is fully released at the end of the release process, (iii) corresponds to a remaining contact area size during the release process or (iv) corresponds to the distance between the stop surface and the flexible medicine reservoir. The output signal can also indicate one or more of these states.

From this output signal, the processing unit determines the fill level of the flexible medicine reservoir. In a simple embodiment, the processing unit is configured to determine whether the fill level has fallen to or below the threshold. The threshold can equal the predetermined fill level, which means that this threshold has been reached when the contact between the stop surface and the flexible medicine reservoir starts to release. Similarly, in some embodiments, the threshold can include a fill level at which the release process ends. This means that the fill level at which the contact area size has just fallen to zero. As another example, the threshold may be located at an intermediate point between the beginning and the end of the contact release process. This is possible if the release detector outputs a signal that corresponds to the actual fill level of the flexible medicine reservoir, for example by an unambiguous, in particular continuous manner. Preferably, the threshold is a fill level that is higher than the empty level at which no medicine is left in the reservoir. For example, the threshold is a fill level which is a certain percentage of the maximum fill level of the reservoir, for example 50%, 25%, 20%, 15%, 10%, 5%, 2% or 1% of the maximum fill level.

This means that in some embodiments, there are actually two fill levels of the flexible medicine reservoir of interest. The first level is the predetermined fill level at which the contact between the stop surface and the reservoir starts being released and the second level is the threshold level, which is an absolute fill level to be detected. As explained above, these two fill levels may coincide.

As an option, the processing unit is configured to take into account information related to the amount of medicine pumped from the flexible medicine reservoir by a pump. This information can be provided by the control unit of the pump. The control unit might be the same as the processing unit for determining the fill level. Preferably, taking the additional information into account starts when the device has determined that the threshold has been reached.

This means that the processing unit starts summing or integrating the amount of pumped medicine once the threshold level has been reached. The fill level of the reservoir is then calculated by subtracting the summed or integrated amount of pumped medicine from the threshold level. In this case, a possibly present integration error as discussed above, resulting, e.g., from difference between the nominal and the actual chamber volume of the pump, is not too critical since the integration only starts at a comparatively low filling level of the reservoir. Thus, the resulting total error is limited. If an interval pump is used, the fill level of the flexible medicine reservoir can generally be determined at any point within the interval, but is preferably determined when the chamber of the pump is completely filled or completely empty.

The present disclosure also relates to an apparatus comprising a flexible medicine reservoir and a device for determining the fill level of the flexible medicine reservoir as explained above. In one embodiment, the release detector is a capacitive sensor that includes a plurality of electrodes. The electrodes may be designed such that the electrical field between the electrodes extends at least partially to the flexible medicine reservoir. The electrical field between the electrodes extending to the flexible medicine reservoir means that at least part of the electrical field extend into the reservoir or at least to the surface of the reservoir. The stop surface can include the surface of the electrodes and/or can include a surface covering the electrodes.

A change of the fill level of the flexible medicine reservoir leads to a decrease of the contact area between the stop surface and the flexible medicine reservoir or an increase in the distance between the stop surface and the flexible medicine reservoir. This results in a changed capacity of the capacitive sensor. From the capacity of the capacitive sensor, the fill level of the flexible medicine reservoir can be determined, for example from a look-up table containing pairs of a capacity and a corresponding fill level or a graph representing the correlation of the capacity and the fill level. The electrodes can be area electrodes. This means that an electrode has a length and a width that are significantly larger than the widths of the conductors connecting the electrode. The electrodes can be plane or have a curved surface.

As an additional example, an electrode may include a plurality of fingers or a meandering conductor. The plurality of fingers may be arranged in parallel, such that the electrode has the shape of a rake. An electrode that is configured as a meandering conductor has a shape of a spiral. If both electrodes have the same shape, either of a rake or a spiral, the electrodes can be intertwined, leading to a capacity that can reliably be detected and analyzed.

In another embodiment, the release detector includes a pressure sensor and/or a force sensor. A force sensor outputs an output signal that corresponds to the force exerted on the sensitive area of the force sensor. A pressure sensor outputs an output signal that corresponds to the force exerted on the sensitive area of the pressure sensor divided by an area size, for example the size of the sensitive area. In some embodiments, the sensitive area of the force or pressure sensor includes the stop surface or is in rigid contact with the stop surface. A force sensor or a pressure sensor may include a foil-like element, which is flexible and therefore easy to place on a surface with arbitrary shape. In some embodiments, the sensor may include a force sensitive resistor.

In still some embodiments, the release detector includes an optical detector. An optical detector comprises at least one light source and at least one light detector. The light source emits light in the visible and/or invisible spectrum onto or along the flexible medicine reservoir and the light detector outputs an output signal indicative of the amount of light received from the light source. In one embodiment, the output signal is a binary signal, indicating whether the light path between the light source and the light detector is obstructed or not. In this embodiment, the optical detector works like a light barrier. In some embodiments, the output signal of the light detector can have a continuous range corresponding to the amount of light received. In this embodiment, intermediate fill levels can be determined, while the first embodiment only allows for detection of a threshold. Preferably, the surface of the flexible medicine reservoir is at least partly covered with a reflective coat for reflecting the light emitted by the light source. The coated area reflects the light of the light source onto the light sensor depending on the fill level of the flexible medicine reservoir.

The release detectors described above, that is the capacitive sensor, the pressure sensor, the force sensor and the optical detector, can provide an output signal covering a continuous range of output values, for example voltages. The range of the output values corresponds to a range of fill levels of the flexible medicine reservoir. The relation can be described by a graph or a look-up table, for example. The fill level of the flexible medicine reservoir can then be determined from the graph or the look-up table.

In one embodiment, the derivation of the output signal of the release detector is calculated. Then, for example, an extremum of this derivation can be found, where the threshold of the fill level preferably is reached when the derivation of the release detector output signal has its extremum. In this example, the release detector is preferably designed such that its output signal changes strongest, which means as a maximum in its derivation, at or close to the threshold of the fill level.

In still some embodiments, the release detector is configured as a switch. In this document, the term "switch" means a device that opens and/or closes an electrical circuit depending on whether the stop surface is in contact with the flexible medicine reservoir or not. For example, the switch can be a micro-switch or a foil switch. As another example, the switch can include a plurality of galvanic contacts on the stop surface and a conducting, for example metalized, surface area of the flexible medicine reservoir. This conducting surface opens and/or closes the electrical connection between the two connectors, depending on the fill level of the flexible medicine reservoir. If the fill level of the flexible medicine reservoir is above the threshold, the conducting surface area contacts both contacts and therefore electrically bridges these contacts. If the fill level falls below the threshold, this electrical bridge is opened.

The stop surface can be flat or curved to adapt the correlation between the output signal and the fill level of the flexible medicine reservoir. If this correlation is represented by a graph, the progression of the graph changes depending on the curvature of the stop surface.

In some embodiments, the stop surface is located on a ram that pushes against the flexible medicine reservoir as long as the flexible medicine reservoir is filled above the predetermined level. The ram pushing against the flexible medicine reservoir means that the ram, or the stop surface located on the ram, is in direct contact with the reservoir for a wide range of fill levels of the reservoir. Preferably, the ram exerts a non-negligible force onto the reservoir and potentially deforms it. In this range, the output signal of the release detector remains basically constant and only starts changing when the stop surface loses contact with the reservoir.

As an option, the ram is arranged within a housing of the medical infusion device such that the flexible medicine reservoir can move the ram. Preferably, the ram is spring-loaded, wherein the spring pushes the ram against the flexible medicine reservoir. Further in some embodiments, there is a mechanical stop limiting the movement of the ram towards the flexible medicine reservoir. With this arrangement, the ram pushes into the flexible medicine reservoir for a wide range of fill levels, without the danger of damaging the reservoir if the fill level is very high.

In some embodiments, the release detector providing the stop surface is a part of a housing that houses the flexible medicine reservoir. This housing may be the housing of the medical infusion device, accommodating not only the flexible medicine reservoir and the device for determining the fill level, but usually also other components like a battery or a pump. Similarly, in some embodiments, the device includes a plurality of release detectors. The plurality of release detectors may be configured to cover different areas of the flexible medicine reservoir, for example by monitoring different sub-areas of the stop surface. For example, the sub-areas form a stop surface that is shaped such that the sub-areas lose contact to the flexible medicine reservoir one after the other when the fill level decreases. The plurality of sub-areas can be monitored by only one type of release detector or two or more types of release detectors.

In some embodiments of the device with a plurality of capacitive sensors, the sensors are arranged in a concentric pattern. This means that a first, innermost sensor is completely or almost completely surrounded by another sensor. An optional third sensor completely or almost completely surrounds these two sensors, and so on. Additionally, the innermost sensor may be located on the ram such that it is the last sensor to lose contact with the flexible medicine reservoir when the reservoir is being emptied.

When a plurality of measurement capacitors is used, two or more of these capacitors can use a shared electrode. The same applies if a plurality of switches is used. In some embodiments, the device also comprises a reference capacitor. The capacity of the capacitive sensor is compared to a known capacity of the reference capacitor, resulting in relative measurement values. With the reference capacitor, environmental factors such as temperature, humidity or electromagnetic distortion may have a reduced impact (or no impact) on the accuracy of the determined fill level. The reference capacitor may be physically located as close to the capacitive sensor as possible, but without causing interference between the capacitors. The reference capacitor can have area, finger-shaped, and/or meandering electrodes.

As an additional option, an electromagnetic shielding for the capacitors can be provided. Additionally, the device may be designed such that the change in the output signal of the release detector is largest around the threshold for the fill level. In this case, the threshold of the fill level is reached when the derivation of the output signal over time has a maximum. Optionally, the device is configured to cause an alert if the fill level of the flexible medicine reservoir reaches a particular level. This particular level can equal the predetermined level or the threshold level.

The present disclosure also relates to a method for determining the fill level of an inflow-less flexible medicine reservoir, comprising determining when a threshold fill level of the flexible medicine reservoir has been reached, determining the amount of medicine taken from the flexible medicine reservoir since the threshold fill level has been reached and calculating the fill level by subtracting the determined amount of medicine taken from the flexible medicine reservoir from the threshold fill level. The threshold level can, but not necessarily must be the predetermined fill level at which a contact between a stop surface and the flexible medicine reservoir starts to release. In particular, a device as described above may be used for implementing the method.

In some embodiments of the method, determining when a threshold fill level is reached is performed based on the output signal of a release detector indicative of the contact between a stop surface and the flexible medicine reservoir being released, wherein the stop surface is designed and arranged such that the stop surface contacts the flexible medicine reservoir while the reservoir is filled above a predetermined level. Similarly, in some embodiments, the processing unit for determining the fill level from the output signal of the release detector is the control unit of the medical infusion device used for controlling the pump.

The present disclosure also relates to a system that includes a device for determining the fill level of a flexible medicine reservoir and a flexible medicine reservoir. Similarly, in some embodiments, the present disclosure relates to a medical infusion device that is configured to receive a flexible medicine reservoir, comprising a device for determining the fill level of the flexible medicine reservoir, as explained above.

Referring now to the drawings, FIG. 1 shows an arrangement in which a release detector 2 is located on a ram 3 which pushes into a flexible medicine reservoir 1 such that a stop surface, which in the present arrangement is a sensitive area of the release detector 2, is in full contact with the flexible medicine reservoir 1 as long as the fill level of the reservoir is above a predetermined fill level. The term "full contact" means that the whole stop surface is in contact with the flexible medicine reservoir.

This arrangement has the advantage that the stop surface remains in contact with the flexible medicine reservoir 1 over a wide range of fill levels. Once the fill level has fallen to a predetermined fill level, the contact of the release detector 2, and therefore of the stop surface, with the surface of the flexible medicine reservoir 1 is gradually released, which means that from this point on, the output signal of the release detector 2 rapidly changes, while output signal was basically constant prior to this point. When the flexible medicine reservoir 1 is empty, the distance between the flexible medicine reservoir 1 and the release detector 2 is denoted with an "e." The parameter e is chosen such that the forces exerted from a full reservoir on the ram and the housing do not get too strong. For miniaturization reasons, a small value for e in the range of typically 1 mm to 5 mm is generally utilized. Other values, however, are possible as well.

Figure 2:
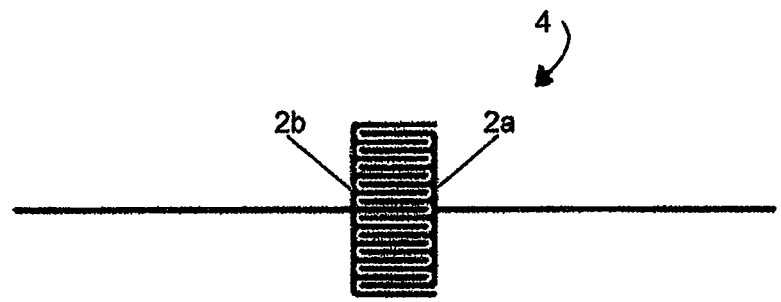
FIG. 2 depicts two rake-shaped electrodes, according to embodiments disclosed herein.
Figure 3:
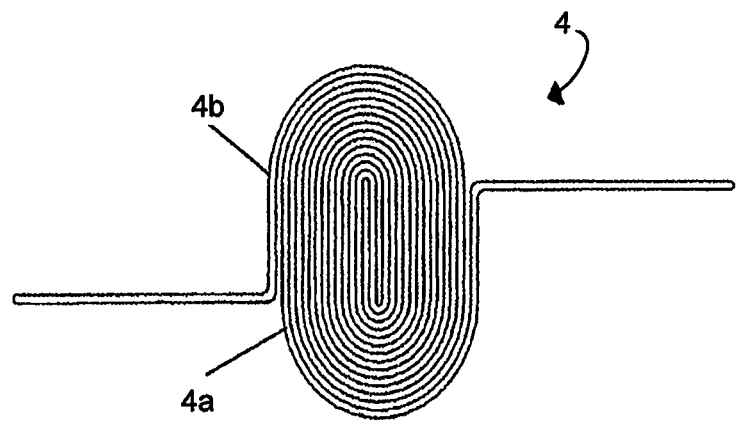
FIG. 3 depicts two meandering electrodes, according to embodiments disclosed herein.

In some embodiments, the release detector 2 is a capacitive sensor 4 that includes the electrodes 2a and 2b and/or 4a and 4b. The electrodes 2a and 2b and/or 4a and 4b are area electrodes covering a closed area with a certain extent in the width and length direction. Similarly, FIGS. 2 and 3 show differing shapes for the electrodes. In FIG. 2, the electrodes 2a and 2b include a plurality of fingers, thus having the shape of rakes. The electrodes 2a and 2b are intertwined such that the distance between the electrodes is small and the fingers are interlocked. In FIG. 3, the electrodes 4a and 4b include meandering conductors, giving the electrodes the shape of a spiral. In this example, the spiral has an oval shape and the electrodes 4a and 4b are intertwined. The conductors forming the electrodes 4a and 4b run parallel.

Figure 4:
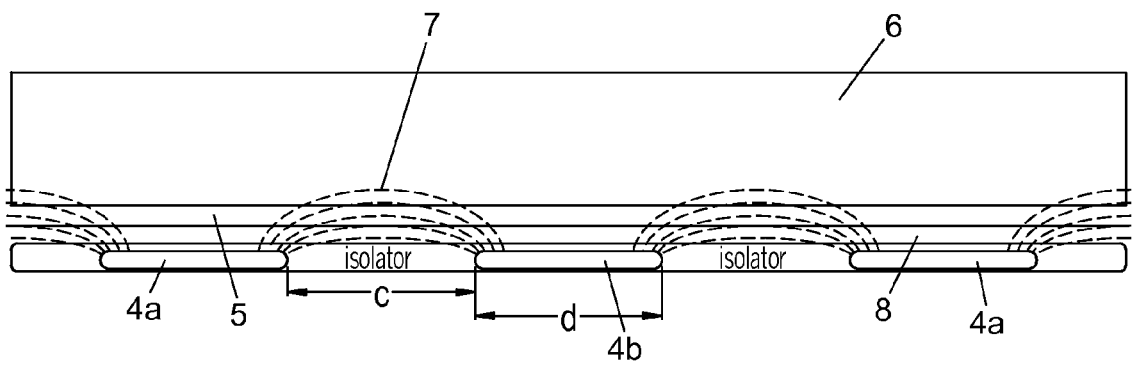
FIG. 4 depicts an electrical field between two electrodes, according to embodiments disclosed herein.

FIG. 4 schematically shows a principle of the device according to the first exemplary embodiment. The flexible medicine reservoir 1 includes a bag 5 filled with insulin 6. The electric flux lines between the electrodes 4a and 4b, which represent the electrical field, are shown as dashed lines 7. At the fill level shown in FIG. 4, the electrical field between the electrodes 4a and 4b extends through a gap 8, e.g. filled with air, into the flexible medicine reservoir 1 such that it passes the bag 5 and the insulin 6. Depending on the fill level of the flexible medicine reservoir 1, the composition of materials in the electrical field between the electrodes 4a and 4b changes, which leads to a capacity of the capacitive sensor 4 depending on the fill level of the flexible medicine reservoir 1.

In the embodiment shown in FIG. 4, the stop surface is the surface of an isolator in which the electrodes 4a and 4b are embedded. However, in some embodiments, the isolator does not cover the electrodes, such that the surface of the electrodes is the stop surface or a part of the stop surface. If the flexible medicine reservoir is filled above a certain fill level, for example the predetermined fill level, the size of the gap 8 is zero, which means that the stop surface is lying flat on the flexible medicine reservoir 1. While the flexible medicine reservoir 1 is emptied, the contact area of the stop surface with the flexible medicine reservoir 1 decreases until the contact is completely lost and there is no more physical contact. From then on, only the width of the gap 8 increases if the reservoir is further emptied.

Figure 5:
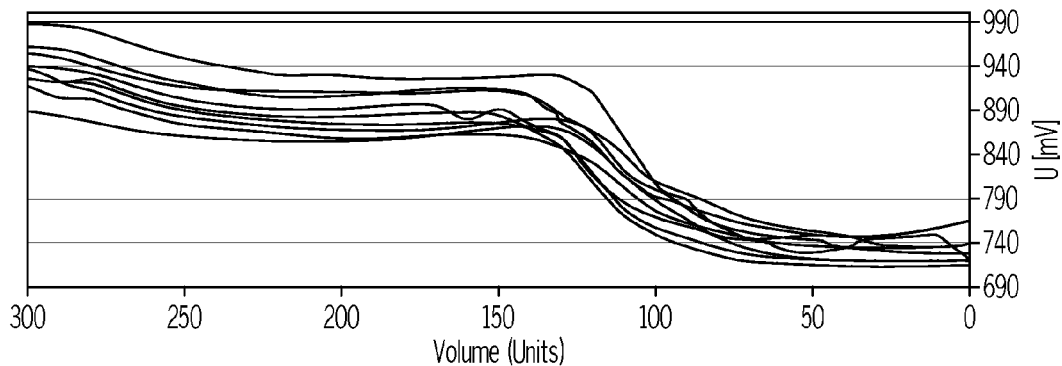
FIG. 5 depicts a measured graph of a voltage corresponding to a capacity over the fill level, according to embodiments disclosed herein.
Figure 7:
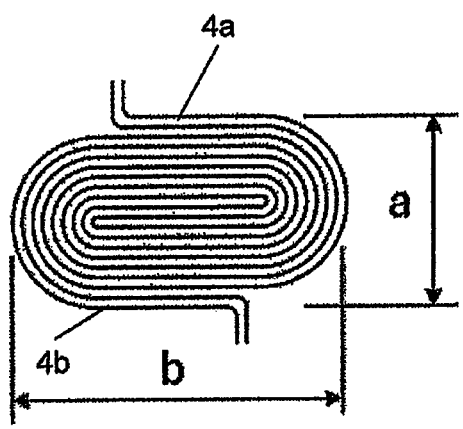
FIG. 7 depicts the dimensions of two intertwined, meandering electrodes, according to embodiments disclosed herein.
Figure 8:
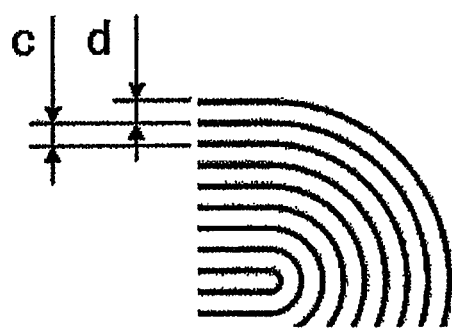
FIG. 8 depicts width of and distance between the electrodes shown in FIG. 7, according to embodiments disclosed herein.

FIG. 5 shows several measured graphs representing a voltage U, which corresponds to the capacity C of the capacitive sensor 4, over the fill level of the flexible medicine reservoir. The fill level V is given in standardized volume units of the medicine, for example insulin. For the graphs shown in FIG. 5, the electrodes as shown in FIG. 3 are arranged on a flat surface of the ram 3 pushing against the reservoir as shown in FIG. 1. As can be seen from FIG. 7, the area covered by the intertwined electrodes 4a and 4b has a width of "a" and a length of "b." As can be seen from FIG. 8, the conductors forming the electrodes 4a and 4b have a width of "d" and are spaced apart by a distance "c." The voltage U is indicated in millivolts (mV). The parameters of the electrodes 4a and 4b leading to the graph shown in FIG. 5 are a=15 mm, b=28 mm, c=0.8 mm, d=0.8 mm and e=1 mm. Examples of parameters of a flexible medicine reservoir include a size of 42×33 mm and a maximum fill level between 100 and 500 units, for example 300 units, for the standard insulin concentration U100.

As can be seen from FIG. 5, the voltage U, and therefore the capacity C of the capacitive sensor 4, remains basically constant up to a point at which the flexible medicine reservoir 1 is emptied to a fill level of about 150 units. From this fill level on, the stop surface loses contact with the surface of the flexible medicine reservoir 1, which means that at least parts of the electrical field between the electrodes extend through air before they reach the reservoir. Further emptying of the reservoir leads to a decrease in capacity C, and therefore of the voltage U, until the gap between the electrodes and the reservoir has reached a size at which the electrical field between the electrodes extends through the air in the most part and only a small amount penetrates the flexible medicine reservoir 1. This happens at a fill level of about 60 units. Further emptying of the reservoir does not further decrease the capacity of the capacitive sensor 4. So this means that only in a fill level range between 150 units and 60 units the capacity C and therefore the voltage U decreases.

Figure 6:
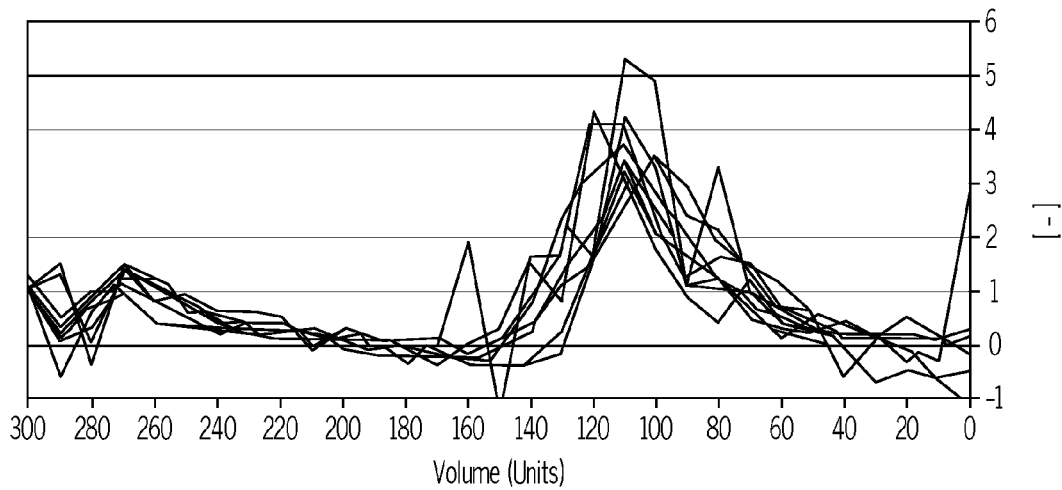
FIG. 6 depicts the derivation of the graph of FIG. 5, according to embodiments disclosed herein.

FIG. 6 depicts the negative derivation of the graphs shown in FIG. 5 over the fill level V of the flexible medicine reservoir 1. It can be seen that all graphs in FIG. 6 have a maximum at about 110 units. This means that the decrease in capacity C at a fill level V of 110 is highest. In some embodiments, the amount of medicine pumped by the pump, which empties the flexible medicine reservoir 1 is taken into account for determining the fill level V starting from a point at which the negative derivation shown in FIG. 6 reaches a peak, for example, a point at which the change in capacity C of the capacitive sensor 4 is highest. The fill level V at which the peak occurs is known, such that this fill level can be used as a starting point for fill level determination using the relative information about the amount of delivered medicine. The fill level can be determined by subtracting the integrated amount of delivered medicine from a threshold fill level, wherein this threshold fill level preferably is the fill level at which the peak in FIG. 13 occurs. Graphs very similar to those shown in FIGS. 5 and 6 result if the capacitive sensor 4 is replaced by a force sensor as the release detector 2 and the ram 3 is spring-loaded.

Figure 9:
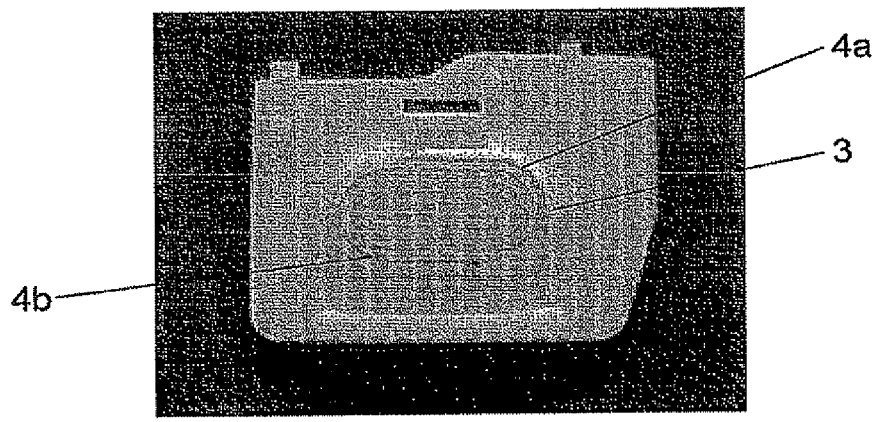
FIG. 9 depicts a ram carrying two electrodes on a flat surface, according to embodiments disclosed herein.
Figure 10:
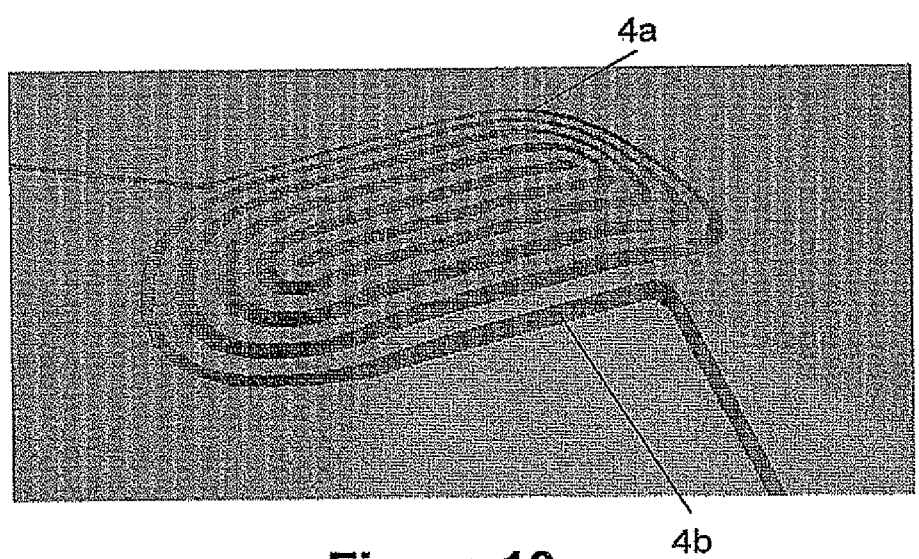
FIG. 10 depicts two electrodes on a curved surface of a ram, according to embodiments disclosed herein.

FIG. 9 shows an exemplary embodiment of a ram 3 carrying the intertwined electrodes 4*a* and 4*b* on a flat portion of its surface. FIG. 10 shows the electrodes 4*a* and 4*b* on a curved surface of the ram. By adjusting the curvature, that is the 3-dimensional shape of the surface carrying the electrodes or of the stop surface when using any type(s) of release detector (s), the progression of the capacity C (or, in general, of the release detector output signal) over the fill level V can be influenced, for example depending on a fill level range at which a particular resolution of the fill level is to be achieved.

Figure 11:
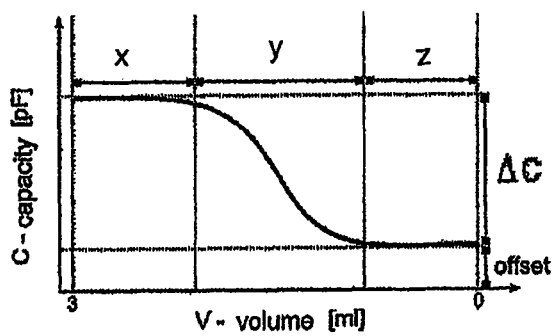
FIG. 11 depicts an idealized curve of the capacity over the fill level, according to embodiments disclosed herein.

FIG. 11 shows a version of the graph shown in FIG. 5, depicting the capacity C of a capacitive sensor 4 over the decreasing fill level V of the flexible medicine reservoir 1. In the fill level range, the flexible medicine reservoir 1 is quite full and the ram 3 with the electrodes 4*a* and 4*b* pushes into the reservoir. In this range, the reservoir remains in contact with the stop surface and the capacity C is therefore basically constant. In the fill level range y, the contact area between the stop surface and the flexible medicine reservoir 1 continuously decreases, generating a distance between the reservoir and the electrodes. In this range, the decrease in capacity is strongest. In the fill level range "z," the distance between the electrodes and the reservoir is so large such that the flexible medicine reservoir 1 as the dielectric has almost no influence on the capacity C.

In FIG. 11, ΔC denotes the maximum difference in capacity which occurs during the measurement, (e.g., between a completely filled and a completely empty reservoir). The term "offset" denotes the minimum capacity C of the capacitive sensor 4, having only air with a permittivity of 1 as the dielectric.

Figure 12:
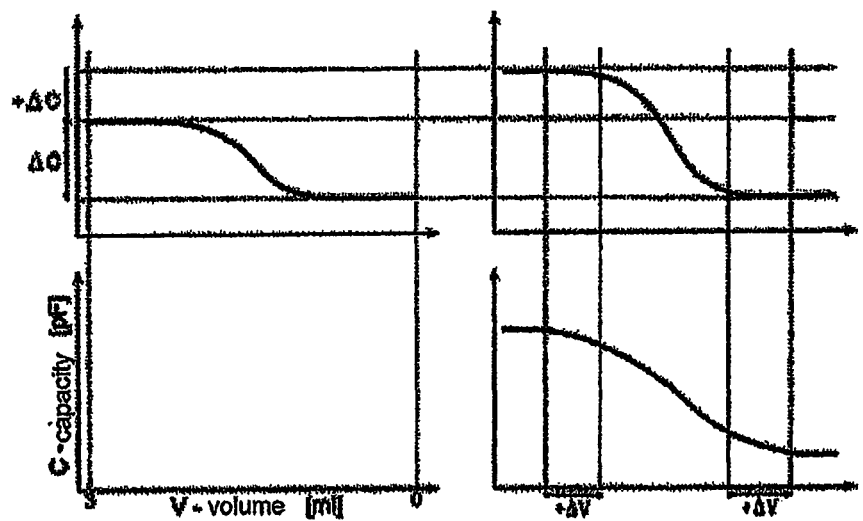
FIG. 12 depicts variations of the graph of FIG. 11, according to embodiments disclosed herein.

FIG. 12 depicts modifications to the graph shown in FIG. 11. In the upper left of FIG. 12, a graph is shown with ΔC as in FIG. 11. In the upper right, ΔC was enhanced by a further +ΔC, which means that the range ΔC of the capacity C of the capacitive sensor 4 is increased. This can, for example, be achieved by reducing the width "d" of the conductor forming the electrodes. From the upper right to the lower right of FIG. 12, the slope of the graph was reduced, (for example, the fill level range "y" as shown in FIG. 11 was expanded). The range "y" is expanded by +ΔV to the left as well as to the right. This can be achieved, for example, by amending the surface curvature of the ram 3 on which the electrodes 4*a* and 4*b* are located.

FIGS. 13*a*-13*d* schematically depict an exemplary embodiment using three capacitive sensors 4, 9 and 10. In this embodiment, each capacitive sensor 4, 9 and 10 has a structure as shown in FIG. 2 and/or a structure as shown in FIG. 3. The capacitive sensor 4 includes the electrodes 4*a* and 4*b*, the capacitive sensor 9 includes the electrodes 9*a* and 9*b* and the capacitive sensor 10 includes the electrodes 10*a* and 10*b*.

Figures 13A, 13B, 13C, 13D:
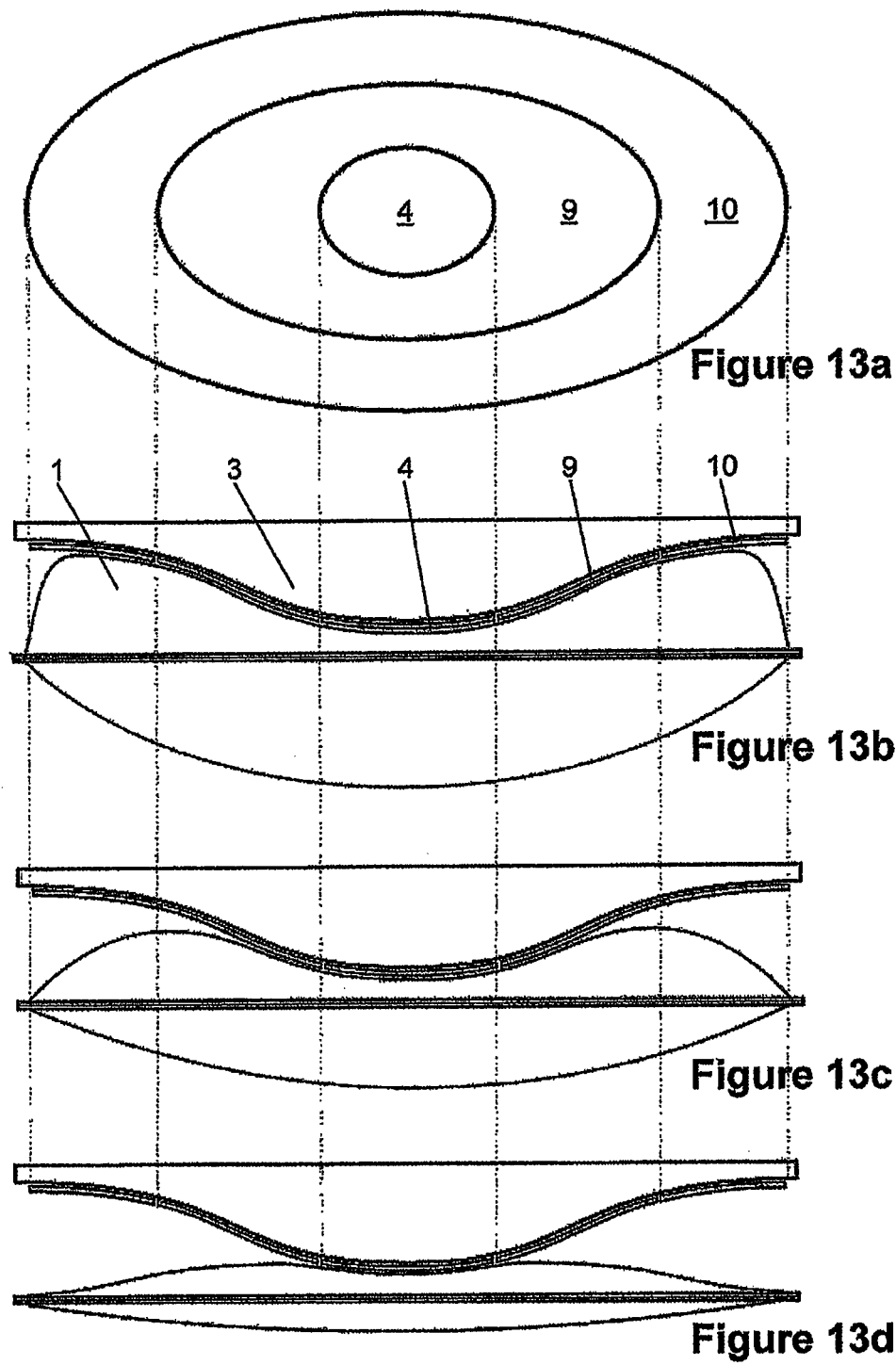
FIGS. 13a-13d depict three concentric measurement capacitors, according to embodiments disclosed herein.

As can be seen from FIG. 13*b*, the capacitive sensors 4, 9, and 10 are located on a ram 3 which has a curved surface. The capacitive sensors 4, 9, and 10 are arranged in a concentric manner, which means that the capacitive sensor 9 surrounds the capacitive sensor 4 and the capacitive sensor 10 surrounds the capacitive sensor 9. In the area in which the capacitive sensor 4 is located, the thickness of the ram 3 is highest. Moving away from the area at which the capacitive sensor 4 is located, the thickness of the ram 3 is gradually reduced.

In the state shown in FIG. 13*b*, the flexible medicine reservoir 1 is completely filled. In this state, the capacitive sensors 4 and 9 are in full contact with the reservoir, while the capacitive sensor 10 is only partly in contact with the reservoir. In the state shown in FIG. 13*c*, the fill level of the flexible medicine reservoir 1 is reduced. In this state, only the capacitive sensor 4 is completely in contact with the reservoir. The capacitive sensor 10 has no contact with the reservoir and the capacitive sensor 9 is only partly in contact with the reservoir.

In the state shown in FIG. 13*d*, the fill level of the flexible medicine reservoir 1 is further reduced. In this state, the capacitive sensor 4 is fully in contact with the reservoir, while the capacitive sensors 9 and 10 have no contact with the reservoir. If the flexible medicine reservoir 1 is further emptied (not shown), also the contact of the capacitive sensor 4 with the flexible medicine reservoir 1 starts to release.

With the configuration as shown in FIG. 13*a*, it is possible to determine the fill level of the flexible medicine reservoir over a large fill level range by analyzing the capacity of all three capacitive sensors 4, 9, and 10. It is apparent that only two or more than three capacitive sensor can be used, and that the arrangement of the plurality of capacitive sensors can be different from the arrangement shown in FIG. 13*a*.

Figure 14:
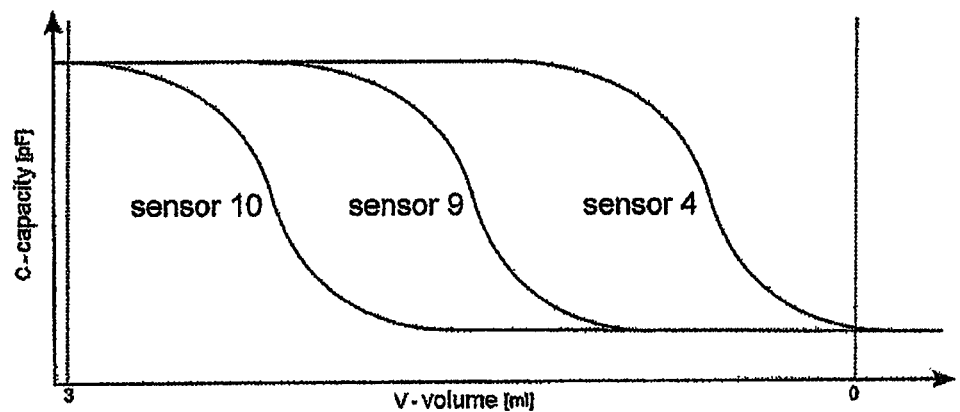
FIG. 14 depicts a curve of the capacity over the fill level for the arrangement of FIGS. 13a-13d, according to embodiments disclosed herein.

The graphs in FIG. 14 show the capacities, which correspond to the output signals, of the capacitive sensors 4, 9, and 10 as shown in FIG. 13. It can be seen that the capacity of the capacitive sensor 10 starts decreasing at a higher fill level than the capacity of the capacitive sensor 9, which in turn starts decreasing at a higher fill level than the capacity of the capacitive sensor 4. With the graphs shown in FIG. 14, the fill level of the flexible medicine reservoir 1 can be determined with high accuracy in a fill level range larger than using only one capacitive sensor.

Figure 15:
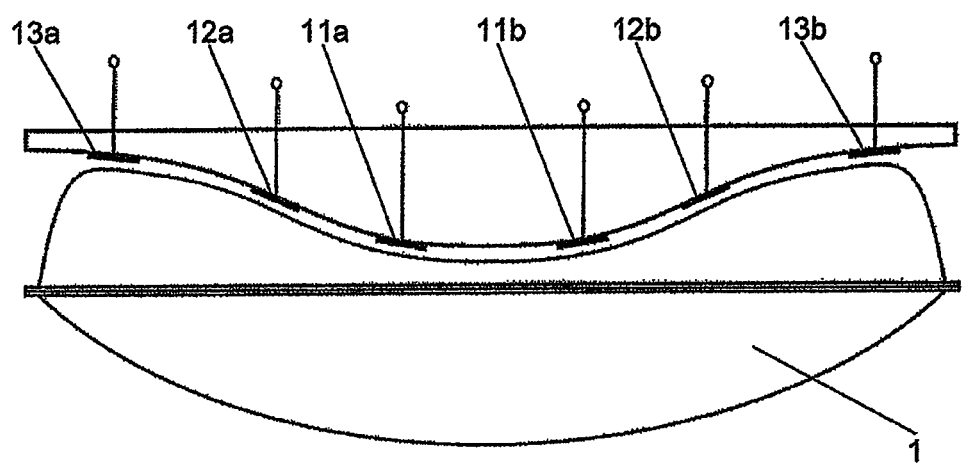
FIG. 15 depicts three concentric galvanic switches, according to embodiments disclosed herein.

FIG. 15 shows a similar arrangement to that in FIG. 13, but using three galvanic switches made up of contacts 11*a* and 11*b*, 12*a* and 12*b*, 13*a* and 13*b*, respectively, as well as an electrically conductive coating on parts of the surface of the flexible medicine reservoir 1. In the state of the flexible medicine reservoir 1 as shown in FIG. 15, all three pairs of contacts 11*a* and 11*b*, 12*a* and 12*b*, as well as 13*a* and 13*b* are electrically shortened by the conductive coating on the reservoir. In analogy to the sequence shown in FIGS. 13*b* to 13*d*, at a certain fill level the contacts 13*a* and 13*b* are not shortened any longer. On further emptying the reservoir, from another fill level on, the contacts 12*a* and 12*b* are not shortened anymore. When the reservoir is yet further emptied, the contacts 11*a* and 11*b* are not shortened anymore. As another embodiment that is similar to the arrangement shown in FIG. 15, the pairs of contacts might be replaced by one common contact and one or more dedicated contact, where a switch is made up of the combination of the common contact and one of the dedicated contacts.

The graph representing the conductivities between the pairs 11*a* and 11*b*, 12*a* and 12*b* as well as 13*a* and 13*b* of conductors over the fill level is similar to the graph shown in FIG. 14, which represents the capacity over the fill level. The difference is that the drop in conductivity is step-like, while the decrease in capacity exhibits a continuous slope. That is, the output signal of the release detectors being switches is binary.

Figure 16A:
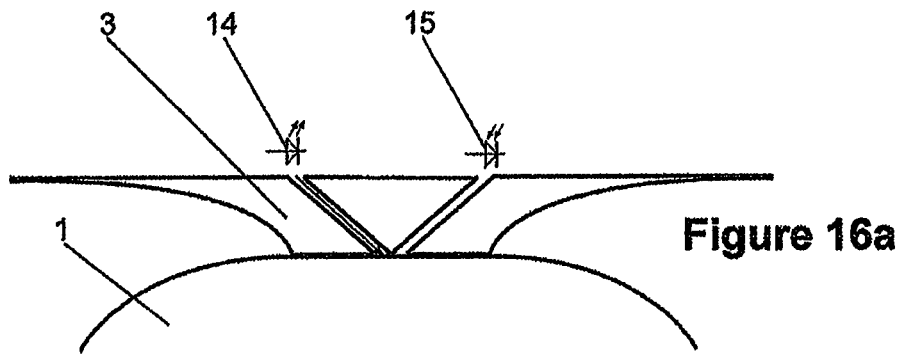
FIGS. 16*a* and 16*b* depict an optical detector as release detector, according to embodiments disclosed herein.

FIG. 16*a* depicts an exemplary embodiment using an optical detector as a release detector. The optical detector includes a light source 14 and a light detector 15, in the present example being a light emitting diode (LED) and a photodiode or a phototransistor, respectively. The light source 14 illuminates a part of the surface of the flexible medicine reservoir 1, for example with light in the visible and/or infrared spectrum. In the state shown in FIG. 16a, in which the stop surface on the ram 3 is in close contact with the flexible medicine reservoir 1, the light emitted from the light source 14 does not reach the light sensor 15.

Figure 16B:
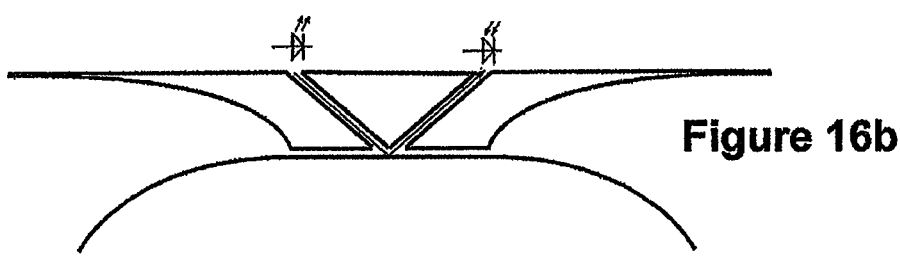

In the state shown in FIG. 16b, with a gap between the ram 3 and the flexible medicine reservoir 1, the light emitted from the light source 14 is reflected by the flexible medicine reservoir 1 and reaches the light detector 15. The output signal of the light detector 15 depends on whether light is reflected onto the detector 15, which is equivalent to whether the ram 3 is in contact with the flexible medicine reservoir 1 or not. The output signal of the light detector 15 can also cover a range of output values depending on the distance between the stop surface and the flexible medicine reservoir 1, thus depending on the amount of light reflected onto the light detector 15.

In the present case, the light source 14 and the light detector 15 are arranged on or in the ram 3 with a distance to the stop surface on the ram 3. Channels in the ram between the light source 14 and the stop surface as well as the stop surface and the light detector 15, respectively, collimate the light and block stray light from influencing the detection result. To further increase the reliability of the detection result, the surface area of the flexible medicine reservoir reflecting the light optionally exhibits a reflective coating.

In some embodiments (not shown), the light source and the light detector form a light barrier monitoring the space between the stop surface and the reservoir. If the stop surface and the reservoir are in contact, the light barrier is interrupted. If they are not in contact, then the light barrier is not interrupted.

Figure 17:
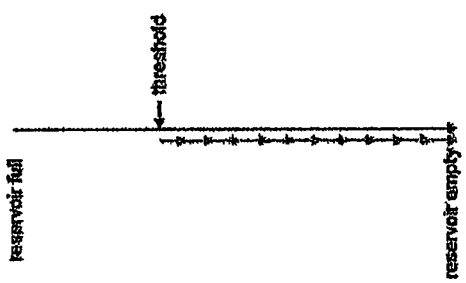
FIG. 17 depicts an illustration of a fill level determining method, according to embodiments disclosed herein.

FIG. 17 illustrates a method for determining the fill level of the flexible medicine reservoir. When the negative derivative of the capacity as shown in FIG. 6 has reached a peak, the fill level of the flexible medicine reservoir 1 has a threshold level, in the example shown in FIGS. 5 and 6 this is a fill level of 110 units. With the release detector 2, this fill level can be reliably determined independent of the fill level of the flexible medicine reservoir 1 when it was inserted into the injection device.

This threshold fill level is then used as an initial fill level or starting fill level from which the amount of medicine pumped by the pump is subtracted. In the example illustrated in FIG. 17, each arrow indicates one pump cycle. In each pump cycle, a piston of the pump moves within a chamber such that a volume of the chamber is increased and the medicine is taken from the flexible medicine reservoir 1. When a certain volume is reached, the piston is pushed such that the size of the chamber decreases and the medicine within the chamber is delivered to a patient. This cycle is then repeated.

Due to the known volume of the pump chamber, the amount of medicine delivered during each cycle is known. The remaining fill level of the flexible medicine reservoir 1 is then the initial fill level detected using the release detector 2 minus the number of pump cycles times the amount of medicine delivered during each cycle. Once the fill level is calculated, a fill level signal may be sent to an output device, control device, and/or other device. As an example, the fill level signal may include an alert that indicates that the fill level has reached a predetermined threshold.

Figure 18:
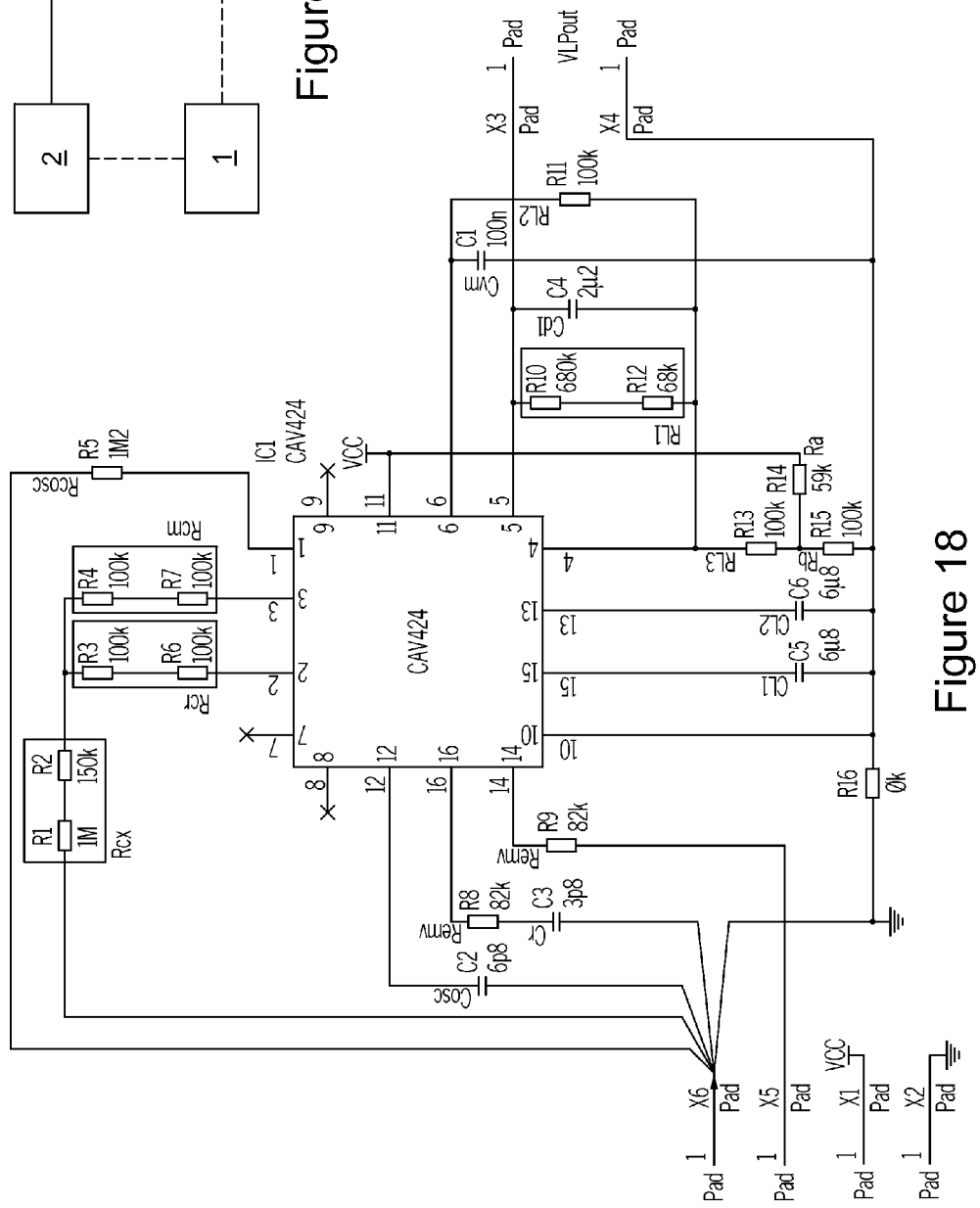
FIG. 18 depicts a circuit for transforming a capacity into a voltage, according to embodiments disclosed herein.

FIG. 18 shows an exemplary circuit diagram of a converter converting the capacity C of the capacitive sensor 4 into an output voltage U. X5 and X6 indicate the connectors for the capacitive sensor 4, X1 and X2 denote the connections for the supply and X3 and X4 denote the output connections for the voltage U. $C_{OSC}$ denotes the reference capacity used for eliminating environmental factors such as temperature, humidity and electromagnetic distortion. $R_{emv}$ denotes a protective circuit against electromagnetic distortion.

Figure 19:
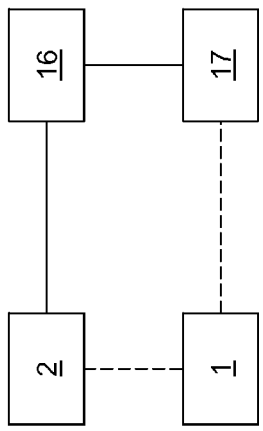
FIG. 19 depicts a schematic block diagram of a medical infusion device, according to embodiments disclosed herein.

FIG. 19 depicts a schematic block diagram of a medical infusion device. The device comprises a processing unit 16, which controls a control device, such as pump 17. The processing unit 16 may be configured as any processor and may be part of a computing device. The processing unit 16 may be configured to execute instructions, such as instructions of a computer program that are stored in a memory component (not shown), such as volatile and/or nonvolatile memory. Additionally, the processing unit 16 may be connected to the release detector 2. The medical infusion device accommodates the flexible medicine reservoir 1. The pump 17 pumps, under the control of the processing unit 16, the contents of the flexible medicine reservoir 1. This is indicated by the dashed line between the pump 17 and the flexible medicine reservoir 1. The release detector 2 is arranged to monitor the contact of the stop surface with the flexible medicine reservoir 1. This is shown by the dashed line between the release detector 2 and the flexible medicine reservoir 1. The processing unit 16 determines the fill level of the flexible medicine reservoir 1 from the output signal of the release detector 2 as explained above. Additionally, while not explicitly illustrated in FIG. 19, the processing unit 16 may additionally be communicatively coupled to an output device, such as a computer monitor, speaker, etc. for providing a fill level signal and/or other output.

FIG. 20 shows an exemplary embodiment of a flexible medicine reservoir 18. The flexible medicine reservoir 18 can replace the flexible medicine reservoir 1. The flexible medicine reservoir 18 may include a rigid wall 20 and an elastic wall 22. The walls 20 and 22 are connected such that they form a volume for the medicine 19. Through an outflow 21 in the rigid wall 20, the medicine 19 can be disbursed. For example, a pump such as pump 17 can be connected to the outflow 21. When a pressure is applied on the flexible medicine reservoir 18, in particular on the flexible wall 22, or if the medicine 19 is pumped out of the flexible medicine reservoir 18, the fill level within the flexible medicine reservoir 18 monotonically decreases.

Figure 21:
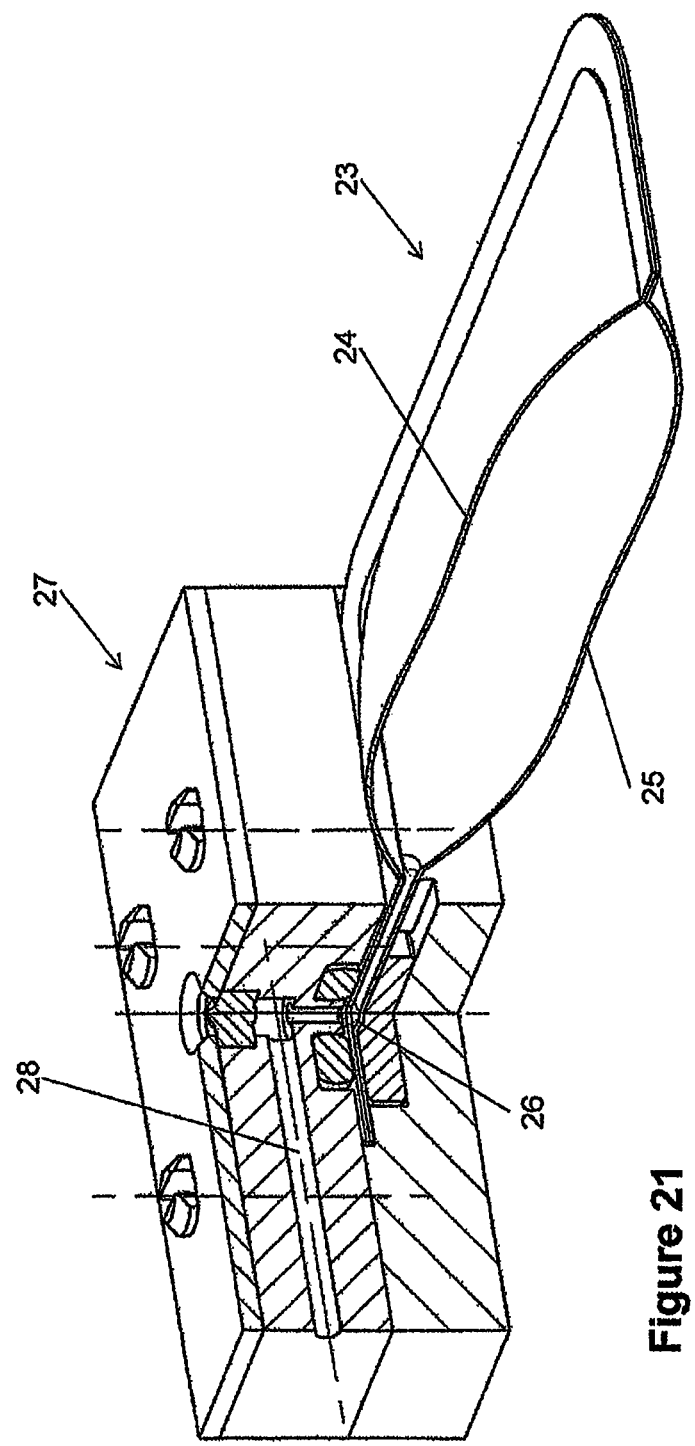
FIG. 21 depicts another exemplary reservoir, according to embodiments disclosed herein.

FIG. 21 shows another exemplary embodiment of a flexible medicine reservoir 23 in a partly cross-sectional view. The flexible medicine reservoir 23 can replace the flexible medicine reservoir 1. It comprises a wall, including two sheets 24 and 25 of flexible, liquid-tight material sealed along a circumferential sealing rim. At a longitudinal end of the flexible medicine reservoir 23, the sealing rim merges with a sealed area where a larger area of the sheets 24 and 25 has been sealed together. An access opening 26 is located at the longitudinal end of the flexible medicine reservoir 23, which is in fluid connection with the storage volume of the reservoir via a fluid channel. The access opening may be embodied as a hole in the wall at the end of the fluid channel opposite to the storage volume, and can be connected to an infusion pump device, either directly or via a connection element 27.

The connection element 27 comprises two clamp parts between which a longitudinal end of the flexible medicine reservoir 23 can be clamped. One clamp part comprises a block with a conduit system 28 and sealing elements for fluidly connecting the access opening 26 with said conduit system 28. A full description of the flexible medicine reservoir 23 and the connection element 27 is given in EP 2 193 815 A1 which is hereby incorporated by reference.

FIG. 22 shows another exemplary embodiment of a flexible medicine reservoir 29, which can replace the flexible medicine reservoir 1. The flexible medicine reservoir 29 comprises two walls 30 and 31 and a port 33 (or outflow), the port being arranged in the center of one of the essentially circularly shaped walls. The walls include a flexible, liquid-tight material sealed along a circumferential sealing rim. The port 33 comprises a flange for mounting the port on the wall 30, an adapter 34 for connecting the port to an infusion pump device and a base plate facing towards the inner storage volume. The base plate is formed by the flange and the longitudinal end of the adapter 34 facing toward the inner storage volume. An inner conduit leads from an outer opening to an inner opening arranged in the center of the base plate. In the shown embodiment, a septum 35 is arranged in the inner conduit. This particular embodiment is thus suitable for use with a hollow needle penetrating the septum to connect the flexible medicine reservoir 29 to an outer conduit system. The flange of the port 33 is connected in a liquid-tight manner to the inner side of the wall 30, for example by ultrasonic welding. A more detailed description of the flexible medicine reservoir 29 is given in document EP 2 179 755 A1, which is hereby incorporated by reference.

Figure 23:
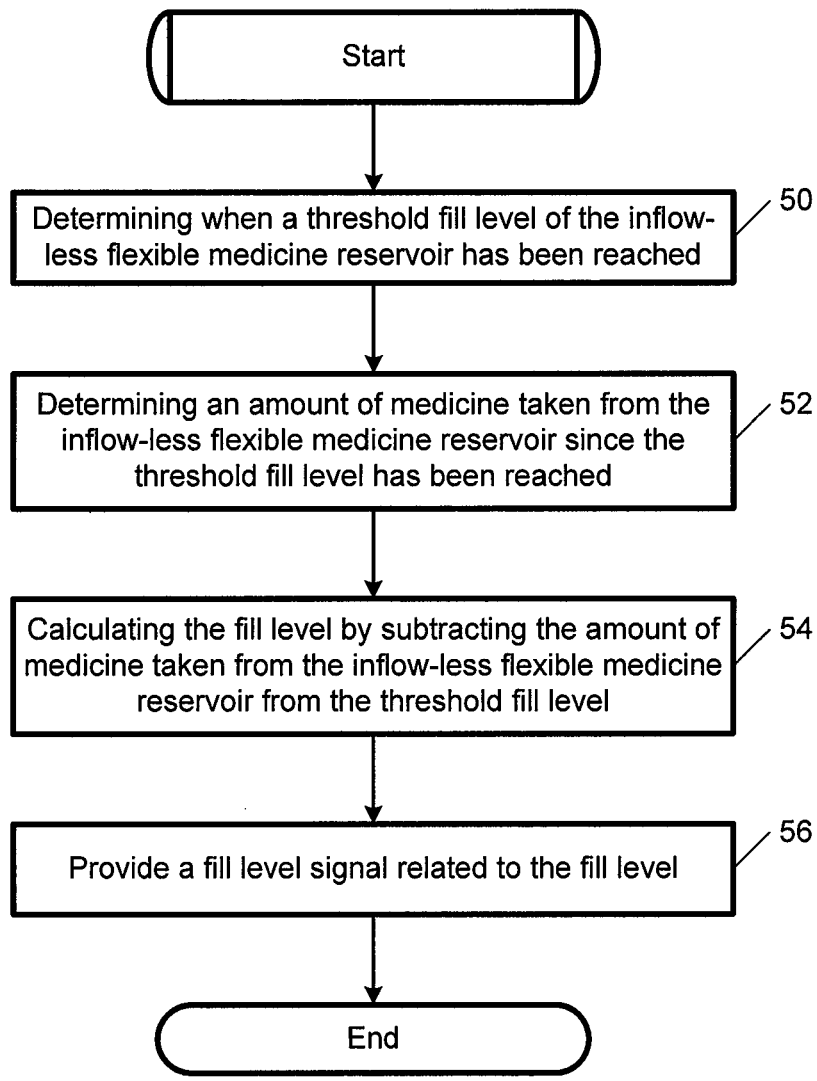
FIG. 23 depicts a flowchart for providing a fill level signal, according to embodiments disclosed herein.

FIG. 23 depicts a flowchart for providing a fill level signal, according to embodiments disclosed herein. As illustrated at block 50, a determination can be made regarding when a threshold fill level of the inflow-less flexible medicine reservoir has been reached. At block 52, a determination can be made regarding an amount of medicine taken from the inflow-less flexible medicine reservoir since the threshold fill level has been reached. At block 54, a calculation may be performed regarding the fill level, where the calculation includes subtracting the amount of medicine taken from the inflow-less flexible medicine reservoir from the threshold fill level. At block 56, a fill level signal may be provided, where the fill level signal is related to the current fill level.

What has been described above are examples of this disclosure. It is, of course, not possible to describe every conceivable combination of components or methodologies, but one of ordinary skill in the art will recognize that many further combinations and permutations of the subject disclosure are possible. Accordingly, the subject disclosure is intended to embrace all such alterations, modifications and variations that fall within the spirit and scope of the claims. Furthermore, to the extent that the term "includes" is used in either the detailed description or the claims, such term is intended to be inclusive in a manner similar to the term "comprising" as "comprising" is interpreted when employed as a transitional word in a claim.

Therefore, at least the following is claimed:

1. A device for determining a fill level of an inflow-less flexible medicine reservoir as a source for medicine, the inflow-less flexible medicine reservoir having a monotonically decreasing fill level, comprising:
   an elastic wall and a rigid wall connected such that a volume intended to contain the medicine is formed;
   an outflow formed in the rigid wall for disbursement of the medicine;
   a stop surface designed and arranged such that the stop surface contacts the inflow-less flexible medicine reservoir while the inflow-less flexible medicine reservoir is filled above a predetermined level;
   a release detector that generates an output signal indicative of contact between the stop surface and the inflow-less flexible medicine reservoir being released; and
   a processing unit that determines the fill level of the inflow-less flexible medicine reservoir from an output signal of the release detector, wherein the processing unit takes into account information on an amount of medicine pumped from the inflow-less flexible medicine reservoir by a pump.

2. The device of claim 1, wherein the release detector is a capacitive sensor that includes a plurality of electrodes.

3. The device of claim 2, wherein at least one of the plurality of electrodes includes at least one of the following: a plurality of fingers and a meandering conductor, and wherein the plurality of electrodes are intertwined.

4. The device of claim 1, wherein the release detector includes at least one of the following: a pressure sensor and a force sensor.

5. The device of claim 1, wherein the release detector includes an optical detector.

6. The device of claim 1, wherein the release detector includes a switch.

7. The device of claim 1, wherein the stop surface is located on a ram that pushes against the inflow-less flexible medicine reservoir as long as the inflow-less flexible medicine reservoir is filled above the predetermined level.

8. The device of claim 1, wherein the stop surface is a part of a housing that houses the inflow-less flexible medicine reservoir.

9. The device of claim 1, comprising a plurality of release detectors.

10. The device of claim 1, wherein the processing unit determines whether the fill level has fallen to or below a threshold.

11. The device of claim 1, wherein the processing unit determines the fill level of the inflow-less flexible medicine reservoir.

12. A device for determining a fill level of an inflow-less flexible medicine reservoir as a source for liquid medicament, the inflow-less flexible medicine reservoir having a monotonically decreasing fill level, comprising:
   a wall comprising two sheets of flexible material sealed together such that a storage volume intended to contain the liquid medicament is defined;
   an access opening located at the longitudinal end of the inflow-less flexible medicine reservoir which provides a fluid connection with the storage volume;
   a stop surface designed and arranged such that the stop surface contacts the inflow-less flexible medicine reservoir while the inflow-less flexible medicine reservoir is filled above a predetermined level;
   a release detector that generates an output signal indicative of contact between the stop surface and the inflow-less flexible medicine reservoir being released; and
   a processing unit that determines the fill level of the inflow-less flexible medicine reservoir from an output signal of the release detector, wherein the processing unit takes into account information on an amount of medicine pumped from the inflow-less flexible medicine reservoir by a pump.

13. The device of claim 12, wherein the release detector is a capacitive sensor that includes a plurality of electrodes.

14. The device of claim 13, wherein at least one of the plurality of electrodes includes at least one of the following: a plurality of fingers and a meandering conductor, and wherein the plurality of electrodes are intertwined.

15. The device of claim 12, wherein the release detector includes at least one of the following: a pressure sensor and a force sensor.

16. The device of claim 12, wherein the release detector includes an optical detector.

17. The device of claim 12, wherein the release detector includes a switch.

18. The device of claim 12, wherein the stop surface is located on a ram that pushes against the inflow-less flexible medicine reservoir as long as the inflow-less flexible medicine reservoir is filled above the predetermined level.

19. The device of claim 12, wherein the stop surface is a part of a housing that houses the inflow-less flexible medicine reservoir.

20. The device of claim 12, comprising a plurality of release detectors.

21. The device of claim 12, wherein the processing unit determines whether the fill level has fallen to or below a threshold.

22. The device of claim 12, wherein the processing unit determines the fill level of the inflow-less flexible medicine reservoir.

23. A device for determining a fill level of an inflow-less flexible medicine reservoir as a source for medicine, the inflow-less flexible medicine reservoir having a monotonically decreasing fill level, comprising:
- a top flexible wall having a port arranged in the center of the top flexible wall;
- a bottom flexible wall sealed to the top flexible wall along a circumferential sealing rim so as to form an inner storage volume between the top flexible wall and the bottom flexible wall;
- an adapter for connecting the port to an infusion pump device;
- a stop surface designed and arranged such that the stop surface contacts the inflow-less flexible medicine reservoir while the inflow-less flexible medicine reservoir is filled above a predetermined level;
- a release detector that generates an output signal indicative of contact between the stop surface and the inflow-less flexible medicine reservoir being released; and
- a processing unit that determines the fill level of the inflow-less flexible medicine reservoir from an output signal of the release detector, wherein the processing unit takes into account information on an amount of medicine pumped from the inflow-less flexible medicine reservoir by a pump.

24. The device of claim 23, wherein the release detector is a capacitive sensor that includes a plurality of electrodes.

25. The device of claim 24, wherein at least one of the plurality of electrodes includes at least one of the following: a plurality of fingers and a meandering conductor, and wherein the plurality of electrodes are intertwined.

26. The device of claim 23, wherein the release detector includes at least one of the following: a pressure sensor and a force sensor.

27. The device of claim 23, wherein the release detector includes an optical detector.

28. The device of claim 23, wherein the release detector includes a switch.

29. The device of claim 23, wherein the stop surface is located on a ram that pushes against the inflow-less flexible medicine reservoir as long as the inflow-less flexible medicine reservoir is filled above the predetermined level.

30. The device of claim 23, wherein the stop surface is a part of a housing that houses the inflow-less flexible medicine reservoir.

31. The device of claim 23, comprising a plurality of release detectors.

32. The device of claim 23, wherein the processing unit determines whether the fill level has fallen to or below a threshold.

33. The device of claim 23, wherein the processing unit determines the fill level of the inflow-less flexible medicine reservoir.

* * * * *

UNITED STATES PATENT AND TRADEMARK OFFICE
CERTIFICATE OF CORRECTION

PATENT NO.         : 8,516,883 B2
APPLICATION NO.    : 13/617948
DATED              : August 27, 2013
INVENTOR(S)        : Gerald Studer Page 1 of 1

It is certified that error appears in the above-identified patent and that said Letters Patent is hereby corrected as shown below:

On the Title Page

(30) Foreign Application Priority Data
"Nov. 11, 2009   (EP).....................09175634" should read
--Nov. 11, 2009   (EP).....................09175634.6--;

In the Specification

Col. 4, Line 4, "or diameter of the footprint are may be significantly larger as" should read
--or diameter of the footprint may be significantly larger as--;

Col. 12, Line 25, "two or more than three capacitive sensor can be used, and that" should read
--two or more than three capacitive sensors can be used, and that--.

Signed and Sealed this
Twenty-fourth Day of June, 2014

Michelle K. Lee
*Deputy Director of the United States Patent and Trademark Office*